US012558271B1

(12) United States Patent
Calame et al.

(10) Patent No.:     US 12,558,271 B1
(45) Date of Patent:         Feb. 24, 2026

(54) FOLDABLE SANITARY NAPKIN

(71) Applicants: Patrick Anthony Calame, Collingwood (CA); Youlando Thompson, Collingwood (CA)

(72) Inventors: Patrick Anthony Calame, Collingwood (CA); Youlando Thompson, Collingwood (CA)

(73) Assignee: Patrick Anthony Calame, Collingwood (CA)

( * ) Notice: Subject to any disclaimer, the term of this patent is extended or adjusted under 35 U.S.C. 154(b) by 0 days.

(21) Appl. No.: 18/999,406

(22) Filed: Dec. 23, 2024

(51) Int. Cl.
*A61F 13/472* (2006.01)
*A61F 13/53* (2006.01)

(52) U.S. Cl.
CPC ...... *A61F 13/472* (2013.01); *A61F 13/47236* (2013.01); *A61F 13/53* (2013.01); *A61F 2013/530007* (2013.01)

(58) Field of Classification Search
CPC .............. A61F 2013/4525; A61F 13/70; A61F 13/505; A61F 2013/4706; A61F 13/4704; A61F 2013/4581; A61F 13/1513; A61F 2013/15406; A61F 13/2022; A61F 13/474; A61F 13/49087
See application file for complete search history.

(56) References Cited

U.S. PATENT DOCUMENTS

| | | | | |
|---|---|---|---|---|
| 4,122,552 A | * | 10/1978 | Tedford | .................... A41B 9/00 604/389 |
| 4,327,732 A | * | 5/1982 | Thinnes | ................. A61F 5/4401 604/374 |
| 4,484,919 A | * | 11/1984 | Sohn | .................... A61F 13/5611 604/358 |
| 4,536,181 A | * | 8/1985 | Cook | .................... A61F 13/474 604/387 |
| 4,596,570 A | * | 6/1986 | Jackson | ................. A61F 13/474 604/387 |
| 4,597,759 A | * | 7/1986 | Johnson | ................. A61F 13/474 604/389 |
| 4,681,577 A | * | 7/1987 | Stern | ....................... A61F 13/47 D24/126 |

(Continued)

FOREIGN PATENT DOCUMENTS

CA         2619574 A1      2/2007

Primary Examiner — Michele Kidwell
(74) Attorney, Agent, or Firm — Argus Intellectual Enterprise LLC; Jordan Sworen; Daniel Enea

(57) ABSTRACT
A foldable sanitary napkin is provided. The sanitary napkin includes a front pad pivotally connected to a rear pad via a living hinge. The front pad can rest in the panty line area of an undergarment, wherein the rear pad extends laterally beyond the front pad to provide enhanced rear coverage. The front pad and the rear pad each include a fluid-permeable top sheet, an acquisition layer, an absorbent core, and a barrier sheet to prevent fluid leakage. The sanitary napkin further includes an odor-controlling material, and a pH-balancing agent integrated into the absorbent cores of both the front and rear pads. The rear pad includes fold lines for compact storage. An adhesive layer on the bottom surfaces of the front and rear pads secures the napkin to the undergarment. The living hinge and perforated line enable optional separation or folding of the rear pad.

10 Claims, 6 Drawing Sheets

(56)                    References Cited

U.S. PATENT DOCUMENTS

| | | | | |
|---|---|---|---|---|
| 4,772,499 | A | * | 9/1988 | Greenway ............. B29C 59/007 |
| | | | | 156/290 |
| 4,946,454 | A | * | 8/1990 | Schmidt ............ A61F 13/47272 |
| | | | | 604/386 |
| 5,167,654 | A | * | 12/1992 | Yang ..................... A61F 5/4401 |
| | | | | 604/367 |
| D368,519 | S | * | 4/1996 | Harrison ...................... D24/125 |
| 5,704,929 | A | * | 1/1998 | Bien .................... A61F 13/474 |
| | | | | 604/387 |
| 7,648,490 | B2 | | 1/2010 | Kuroda et al. |
| 7,686,792 | B2 | * | 3/2010 | Bell ..................... A61F 13/474 |
| | | | | 604/385.03 |
| 8,317,769 | B2 | | 11/2012 | Kurihara |
| 8,777,913 | B2 | * | 7/2014 | Schneider ............ A61F 13/551 |
| | | | | 604/385.01 |
| 11,369,529 | B2 | | 6/2022 | Stefu et al. |
| 11,554,052 | B2 | | 1/2023 | Mason, Jr. et al. |
| 11,633,312 | B2 | | 4/2023 | Munakata et al. |
| 11,684,521 | B2 | * | 6/2023 | Nguyen ................. A61L 15/26 |
| | | | | 128/885 |
| 11,813,153 | B2 | | 11/2023 | Vohwinkel et al. |
| 2002/0138055 | A1 | * | 9/2002 | Motta ................... A61F 13/474 |
| | | | | 604/385.01 |
| 2003/0135188 | A1 | * | 7/2003 | Yoshimasa ............. A61F 13/82 |
| | | | | 604/385.03 |
| 2008/0009818 | A1 | * | 1/2008 | Rubio ............. A61F 13/47236 |
| | | | | 604/385.01 |
| 2008/0167634 | A1 | | 7/2008 | Kouta et al. |
| 2011/0257619 | A1 | * | 10/2011 | Tosado ............... A61F 13/4758 |
| | | | | 604/385.16 |
| 2013/0060221 | A1 | * | 3/2013 | Popp ...................... A61F 13/82 |
| | | | | 604/385.05 |
| 2016/0228304 | A1 | | 8/2016 | Orechva |
| 2017/0239102 | A1 | * | 8/2017 | Lee ...................... A61F 13/474 |
| 2020/0281781 | A1 | | 9/2020 | Serrano et al. |
| 2020/0315863 | A1 | * | 10/2020 | Kuo ................. A61F 13/49473 |
| 2023/0121410 | A1 | | 4/2023 | Kim |

* cited by examiner

FOLDABLE SANITARY NAPKIN

BACKGROUND OF THE INVENTION

The present invention relates to sanitary napkins. The present invention provides a sanitary napkin having a front pad pivotally connected to a rear pad, wherein the rear pad is configured to cover the buttocks of a wearer.

Sanitary napkins are essential for menstrual hygiene, providing absorbent protection for women during menstruation. These products have evolved over time to address various user needs, including comfort, absorbency, and leak prevention. Conventional sanitary napkins are typically designed with a front pad that fits snugly within the panty line area. However, many users experience challenges with heavy menstrual flow, particularly at night, where traditional designs fail to provide adequate rear coverage. This often leads to leaks, discomfort, and the need for frequent garment changes, which can be both inconvenient and distressing.

Existing sanitary napkins with extended rear coverage attempt to address this issue but come with significant shortcomings. For example, many of these products lack flexibility in design, making them uncomfortable or impractical for daytime use. The rigid connection between the front and rear pads in some designs can also create bulkiness, reducing wearability and causing irritation. Additionally, some extended-coverage napkins use materials or configurations that fail to adequately manage odor, a common concern for users. Other designs compromise compactness, making them less portable and harder to store discreetly.

Another challenge faced by users is the difficulty in customizing sanitary napkins to individual preferences. For instance, while extended rear coverage is beneficial during heavy flow or nighttime use, not all users require or desire this feature during lighter flow periods or in more active situations. Existing designs do not provide the option to modify or remove the extended rear section, limiting their versatility. Furthermore, few existing products incorporate advanced features like pH-balancing agents or effective odor control mechanisms, leaving many user needs unaddressed. Therefore, there exists a need for a sanitary napkin having a T-shape that minimizes odor and promotes pH balance without sacrificing ease of use or portability.

In light of the devices disclosed in the known art, it is submitted that the present invention substantially diverges in design elements and methods from the known art and consequently it is clear that there is a need in the art for an improvement for a sanitary napkin. In this regard the instant invention substantially fulfills these needs.

SUMMARY OF THE INVENTION

In view of the foregoing disadvantages inherent in the known types of sanitary napkins now present in the known art, the present invention provides a new sanitary napkin having a front pad pivotally connected to a T-shaped rear pad configured to cover the buttocks of a wearer.

It is an objective of the present invention to provide a foldable sanitary napkin comprising a rear pad that is wider than the front pad, offering increased surface area to prevent leaks during nighttime use or heavy-flow days. This configuration provides coverage for both the panty line and buttocks areas, minimizing the risk of garment staining and discomfort.

It is an objective of the present invention to provide a foldable sanitary napkin with a customizable design for versatile use. The rear pad is pivotally connected to the front pad via a living hinge, allowing the rear pad to be folded underneath or detached along a perforated line (such as shown in FIG. 6). This feature enables the user to adapt the napkin to different flow levels and activity preferences, enhancing convenience and usability.

It is an objective of the present invention to provide a foldable sanitary napkin that ensures maximum fluid retention and comfort. The invention incorporates an absorbent core in both the front and rear pads, with the rear pad featuring a higher retention capacity to manage heavier flow. The addition of a soft, fluid-permeable top sheet and a barrier sheet ensures that the napkin remains comfortable to wear while preventing fluid leakage.

It is an objective of the present invention to provide a foldable sanitary napkin with advanced odor and hygiene management. The sanitary napkin integrates odor-controlling materials and a pH-balancing agent within the absorbent core to address menstrual odor and maintain a healthy skin environment. These features improve user confidence and comfort throughout wear.

It is an objective of the present invention to provide a foldable sanitary napkin that is compact and easy to store. Fold lines in the rear pad allow the napkin to be folded into a compact configuration for discreet carrying and storage. This enhances portability and ensures the product meets the demands of modern, on-the-go lifestyles.

It is therefore an object of the present invention to provide a new and improved foldable sanitary napkin that has all of the advantages of the known art and none of the disadvantages.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings.

DETAILED DESCRIPTION OF THE INVENTION

Reference is made herein to the attached drawings. For the purpose of presenting a brief and clear description of the present invention, the preferred embodiment will be discussed as used for providing a T-shaped sanitary napkin. The figures are intended for representative purposes only and should not be considered to be limiting in any respect.

Figure 1:
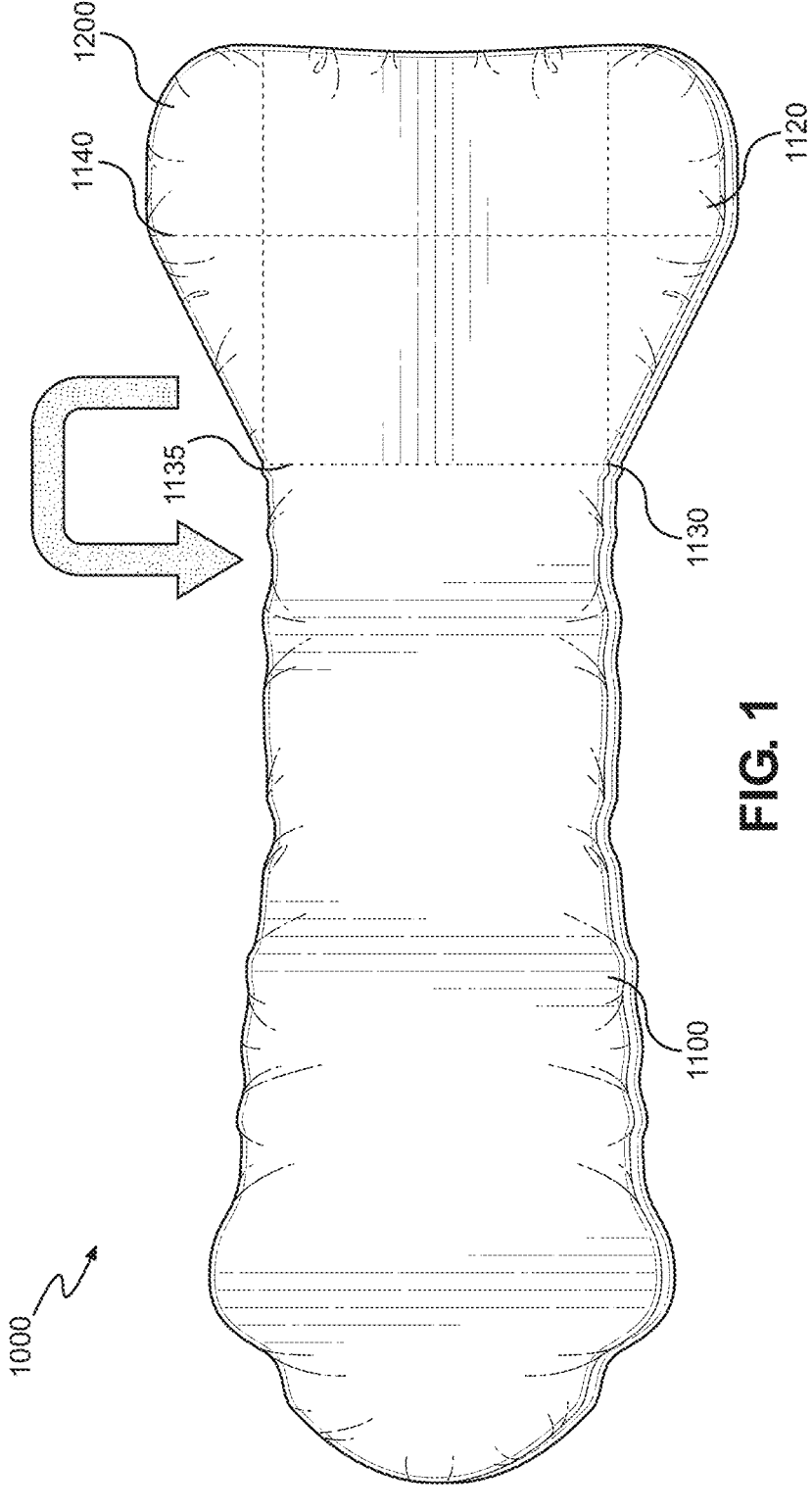
FIG. 1 shows a perspective view of an embodiment of the foldable sanitary napkin.
Figure 2:
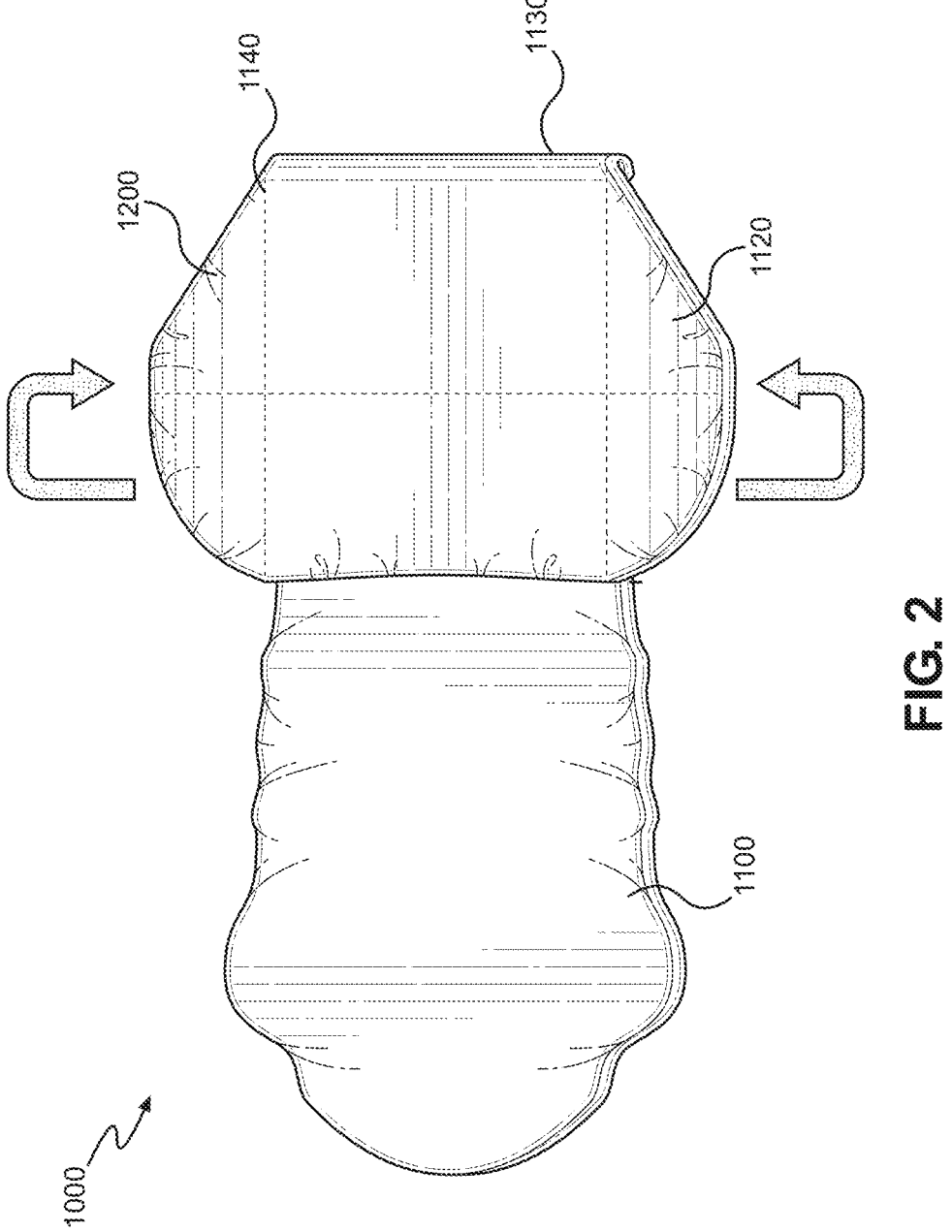
FIG. 2 shows a perspective view of an embodiment of the foldable sanitary napkin in a folded configuration.

Referring to FIGS. 1 and 2, there is shown a perspective view of an embodiment of the foldable sanitary napkin and a perspective view of an embodiment of the foldable sanitary napkin in a folded configuration, respectively. The sanitary napkin 1000 comprises a front pad 1100 and a rear pad 1120 pivotally connected via a living hinge 1130. The front pad 1100 is configured to rest in the panty line area of an undergarment, while the rear pad 1120 is configured to extend to the rear side of the undergarment, covering the buttocks of the wearer. The configuration of the rear pad 1120 includes a pair of lateral extensions 1200 that provide enhanced coverage, particularly for heavy menstrual flow.

The living hinge 1130 enables pivotal movement between the front pad 1100 and the rear pad 1120. In some embodiments, the sanitary napkin comprises a perforated line 1135 disposed along the living hinge 1130, allowing the user to separate the rear pad 1120 from the front pad 1100, if desired. The perforated line 1135 is designed to allow manual separation without the need for tools, thereby increasing the versatility of the sanitary napkin. In the illustrated embodiment, the perforated line 1135 separates the layers of the front pad from the layers of the rear pad, such that fluid does not flow therebetween. In alternate embodiments, the perforated line does not separate the layers of the front pad from the rear pad, entirely, allowing fluid to flow therethrough.

In the illustrated embodiment, the rear pad 1120 includes a plurality of fold lines 1140 that allow it to be folded onto itself into a compact shape. In some embodiments, the fold lines are formed by indicia disposed on a top layer. In other embodiments, the fold lines are formed by thinner material positioned along the fold lines, allowing the pads to fold therealong. This configuration is particularly useful for discreet storage or for instances when the rear pad 1120 is not required for use. In this folded state, the rear pad 1120 can also be positioned underneath the front pad 1100, reducing the overall size of the napkin while maintaining attachment to the undergarment. Additionally, the lateral extensions 1200 of the rear pad 1120 are designed to fold seamlessly along the fold lines 1140, ensuring that the folded configuration remains compact and unobtrusive. When unfolded, the rear pad 1120 resumes its original form to provide full coverage and protection.

Figure 3:
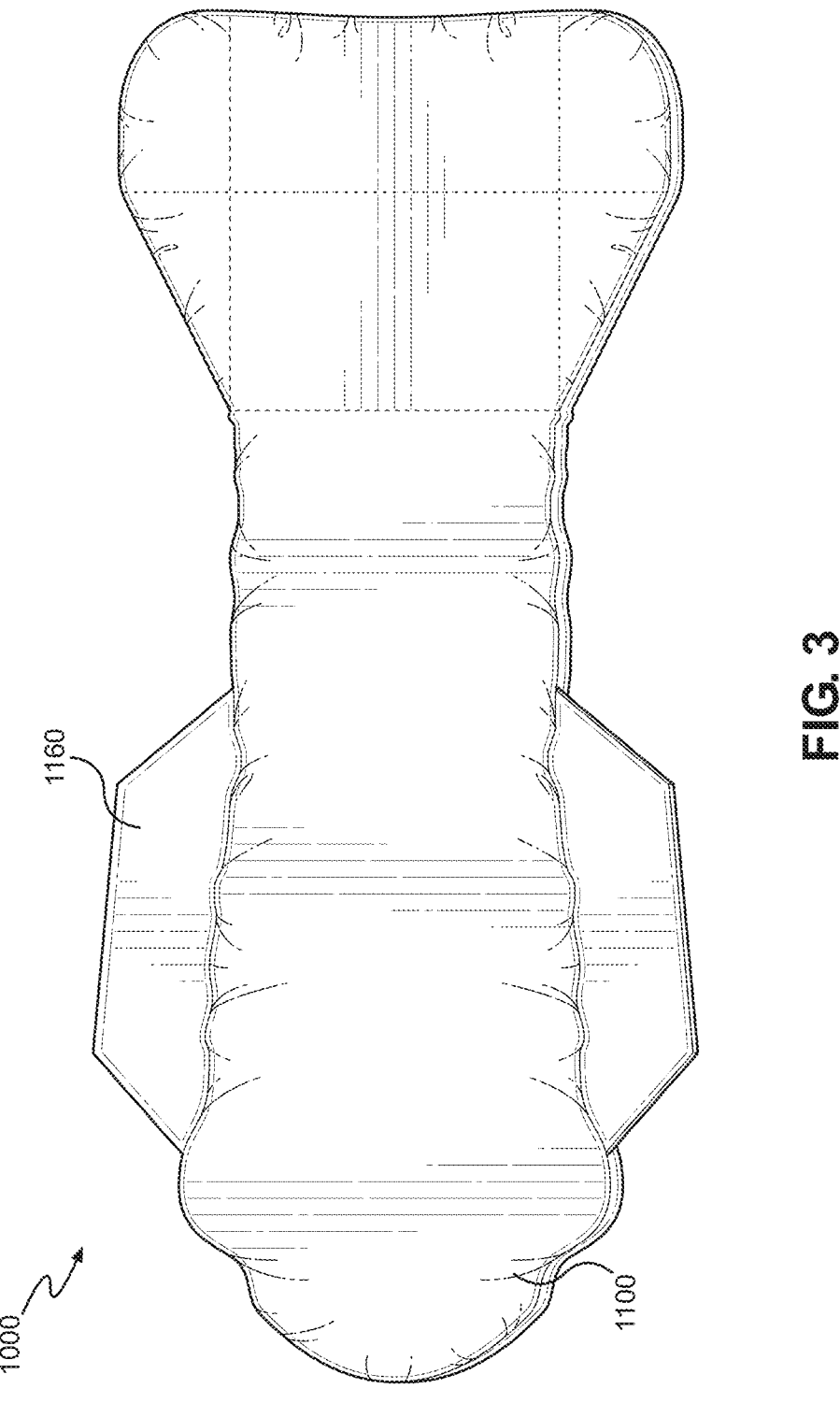
FIG. 3 shows a perspective view of an alternate embodiment of the foldable sanitary napkin.

Referring now to FIG. 3, there is shown a perspective view of an alternate embodiment of the foldable sanitary napkin. In the illustrated embodiment, the foldable sanitary napkin 1000 comprises a pair of wings 1160 extending laterally from the front pad 1100. The wings 1160 are thin and flexible, configured to enhance the securement of the sanitary napkin to the undergarment, particularly during periods of high activity or extended wear. The wings 1160 are integrally formed with the front pad 1100 and are configured to wrap around the edges of the undergarment, ensuring that the sanitary napkin remains firmly in place. Each wing 1160 includes an adhesive strip on its underside, allowing the user to attach the wings to the underside of the undergarment. This configuration prevents the sanitary napkin from shifting or bunching during use, thereby providing improved stability and comfort. In the illustrated embodiment, the wings 1160 are only disposed along the lateral sides of the front pad and mirror one another. In alternate embodiments, the wings are larger and extend from the front pad to the rear pad.

In this embodiment, the wings 1160 are constructed from a fluid-resistant barrier material as the barrier sheet as of the front pad 1100. In this way, the wings 1160 are configured to maintain durability and resist moisture exposure, preventing fluid transfer to the undergarment or surrounding surfaces. The wings 1160 are configured to fold flat against the bottom surface of the front pad 1100 when not in use, allowing the sanitary napkin to be packaged and stored in a compact configuration.

Figure 4:
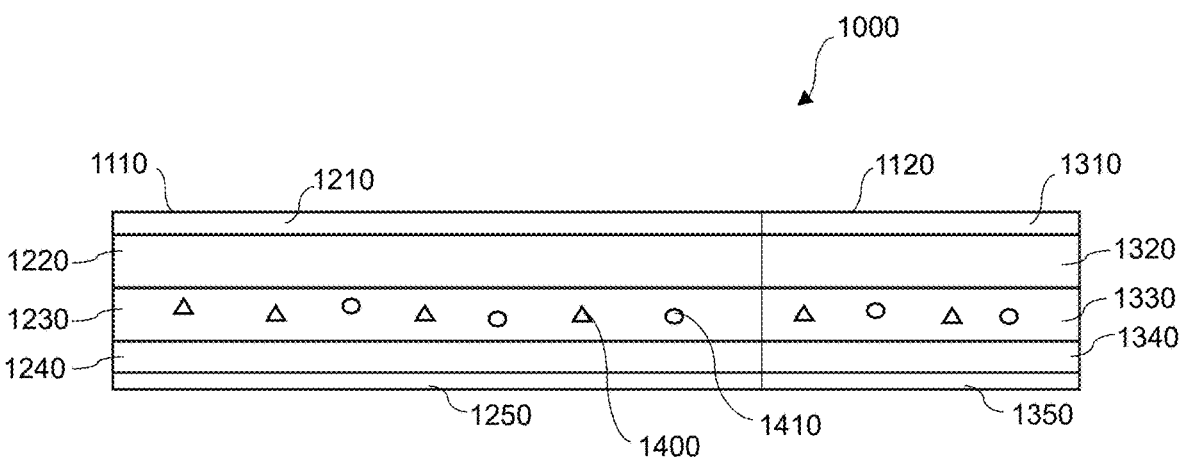
FIG. 4 shows a view of multiple layers of an embodiment of the foldable sanitary napkin.

Referring now to FIG. 4, there is shown a view of multiple layers of an embodiment of the T-shaped sanitary napkin. In the illustrated embodiment, the front pad includes a top sheet 1210 made of a fluid-permeable material for direct contact with the skin. Beneath the top sheet 1210, there is an acquisition and distribution layer 1220 configured to evenly distribute fluid to an absorbent core 1230. The absorbent core 1230 is adapted to retain menstrual fluid effectively, and a barrier sheet 1240 is disposed beneath the absorbent core 1230 to prevent fluid from leaking onto the undergarment. An adhesive layer 1250 is located on the bottom surface of the front pad for secure attachment to the undergarment.

Figure 5:
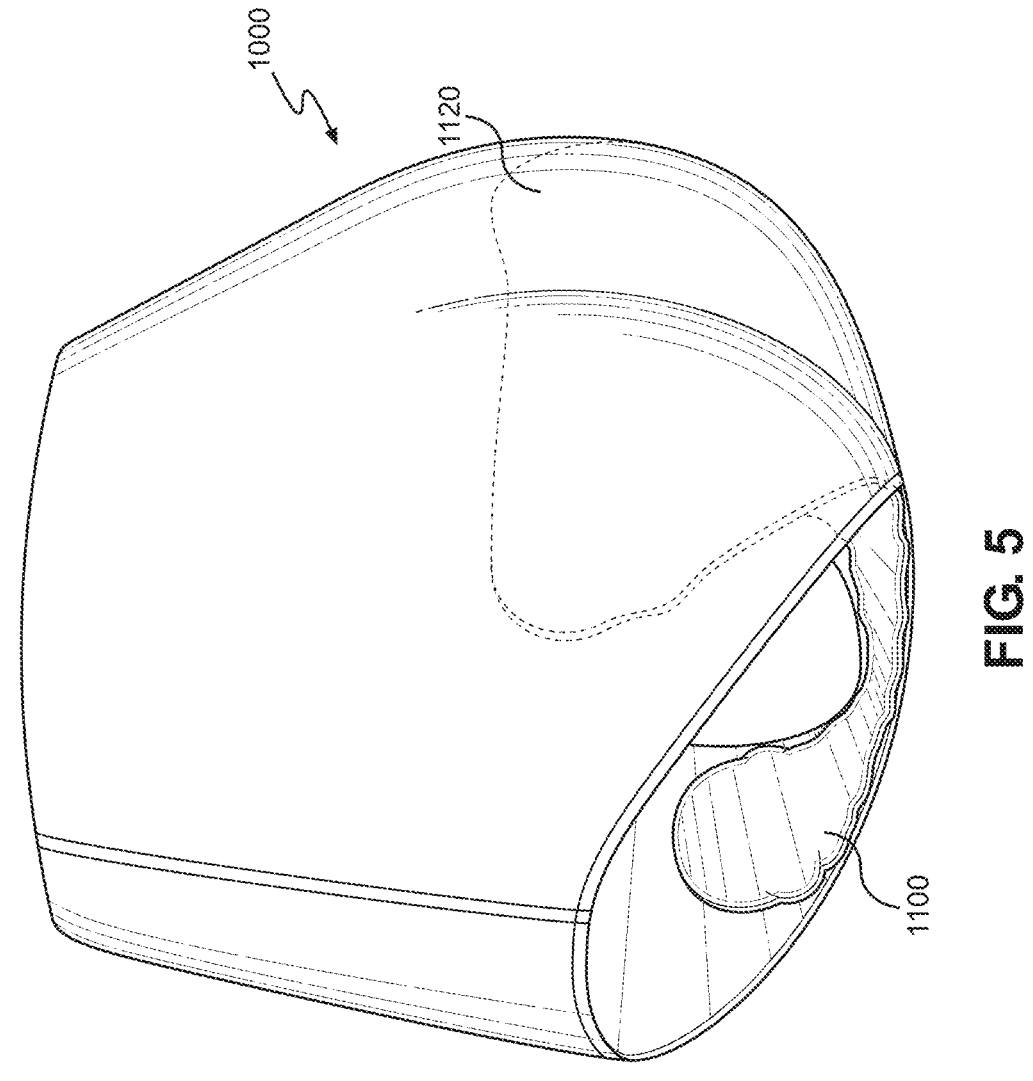
FIG. 5 shows a perspective view of an embodiment of the foldable sanitary napkin in use.

Referring now to FIG. 5, there is shown a perspective view of an embodiment of the foldable sanitary napkin in use. In operation, the adhesive side of the front pad 1100 is positioned within the panty line area of the undergarment, wherein the rear pad 1120 is positioned on the seat or back panel of the undergarment. The pair of lateral extensions are configured to extend to the lateral perimeter of the seat of the undergarment. The lateral extensions 1200 conform to the natural contours of the wearer's body, allowing the pad to rest securely against the undergarment while covering the majority of the buttocks area. This configuration ensures comprehensive fluid retention, even during periods of movement or prolonged wear. The terminal end of the rear pad, opposite the front end of the front pad, is flat and straight to align or conform to an upper edge of the undergarment. In this way, the rear pad is prevented from extending beyond the upper edge of the undergarment.

Figure 6:
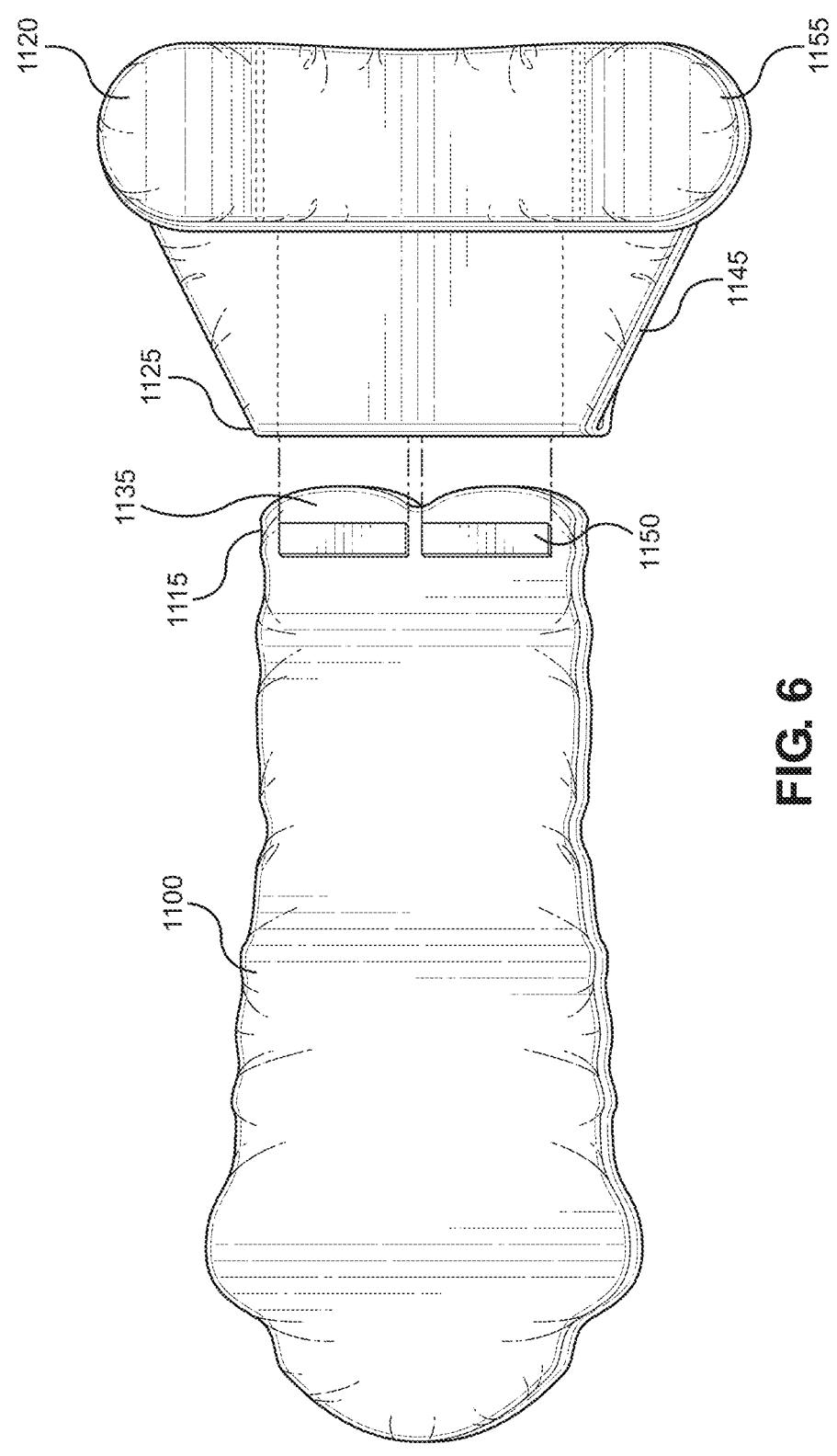
FIG. 6 shows a perspective view of an alternate embodiment of the foldable sanitary napkin, wherein the front pad is detached from the rear pad.

Referring now to FIG. 6, there is shown a perspective view of an alternate embodiment of the foldable sanitary napkin, wherein the front pad is detached from the rear pad. In the illustrated embodiment, the rear pad 1120 is detachable from the front pad 1100 to allow the user to selectively wear the front pad 1100 with or without the rear pad 1120. The rear end 1115 of the front pad 1100 comprises a pair of adhesive strips 1150 that removably secure to the underside of the rear pad 1200, at a front end 1125 thereof. Once the rear pad 1200 is separated from the front pad 1100, a pair of tabs 1135 formed at the rear end 1125 of the front pad 1100 are configured to be folded over onto the adhesive strips 1150. In this way, the adhesive strips 1150 are entirely covered by the rear end of the front pad when not in use to secure to the rear pad 1200.

In the illustrated embodiment, the front end 1125 of the rear pad 1200 is flat to form a continuous surface with the front pad 1100. The lateral sides 1145 of the rear pad 1200 flare outwards to a thicker padded portion 1155, comprising an oblong shape. In this way, the thicker padded portion 1155 of the rear pad 1200 is configured to absorb liquid that passes to the rear side of the undergarment.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, system and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A sanitary napkin, comprising:
a front pad configured to rest in a panty line area of an undergarment of a wearer;
a rear pad pivotally connected to the front pad via a living hinge;
wherein the front pad and the rear pad each comprise:
a fluid-permeable top sheet layer, wherein a top sheet is configured to rest against the wearer;
an acquisition layer configured to distribute fluid evenly within the sanitary napkin;
an absorbent core adapted to retain menstrual fluid;
a barrier sheet disposed beneath the absorbent core to prevent fluid leakage;
wherein the rear pad adapted to rest on a rear side of the undergarment to cover a buttocks of the wearer;
wherein the rear pad is wider than the front pad to accommodate heavy menstrual flow and reduce odor associated with menstruation;
wherein the rear pad comprises a pair of lateral extensions configured to extend laterally beyond a width of the front pad;
wherein a perforated line is disposed transversely along the living hinge and extends substantially across a width of the living hinge between the front pad and the rear pad, the perforated line configured to permit manual separation of the rear pad from the front pad;
wherein the rear pad further comprises a plurality of fold lines disposed on the pair of lateral extensions, the fold lines configured to facilitate folding of the rear pad into a compact configuration wherein the rear pad is folded underneath the front pad;
an adhesive layer disposed on one or more bottom surfaces of each of the front pad and the rear pad for secure attachment to the undergarment.

2. The sanitary napkin of claim 1, wherein the front pad comprises wings configured to fold over the undergarment and secure the sanitary napkin thereto.

3. The sanitary napkin of claim 1, further comprising an odor-controlling material integrated into at least one of the front pad or the rear pad.

4. The sanitary napkin of claim 1, further comprising a pH-balancing agent disposed within the absorbent material of the front pad and/or the rear pad.

5. The sanitary napkin of claim 1, wherein the living hinge comprises a flexible material enabling pivotal movement between the front pad and the rear pad.

6. The sanitary napkin of claim 1, wherein the absorbent core of the rear pad is configured to receive a higher volume of fluid than the absorbent core of the front pad.

7. The sanitary napkin of claim 1, wherein the absorbent core is made of superabsorbent polymers (SAP) combined with fluff pulp for maximum fluid retention.

8. The sanitary napkin of claim 1, wherein the rear pad includes fold lines to facilitate folding into a compact configuration.

9. The sanitary napkin of claim 1, wherein each of the plurality of fold lines is formed by a region of material having a thickness less than a thickness of an adjacent portion of the rear pad, the region of thinner material extending along an entire length of each said fold line.

10. A sanitary napkin, consisting of:
a front pad configured to rest in a panty line area of an undergarment of a wearer;
a rear pad pivotally connected to the front pad via a living hinge;
wherein the front pad and the rear pad each comprise:
a fluid-permeable top sheet layer, wherein a top sheet is configured to rest against the wearer;
an acquisition layer configured to distribute fluid evenly within the sanitary napkin;
an absorbent core adapted to retain menstrual fluid;
a barrier sheet disposed beneath the absorbent core to prevent fluid leakage;
wherein the rear pad adapted to rest on a rear side of the undergarment to cover a buttocks of the wearer;
wherein the rear pad is wider than the front pad to accommodate heavy menstrual flow and reduce odor associated with menstruation;
wherein the rear pad comprises a pair of lateral extensions configured to extend laterally beyond a width of the front pad;
wherein a perforated line is disposed along the living hinge, the perforated line configured to permit manual separation of the rear pad from the front pad;
wherein the rear pad further comprises a plurality of fold lines disposed on the pair of lateral extensions, the fold lines configured to facilitate folding of the rear pad into a compact configuration wherein the rear pad is folded underneath the front pad;
wherein the fold lines of the rear pad define at least two segments that fold to achieve the compact configuration;
wherein an entire length of each fold line is composed of a material thinner than a material of the surrounding rear pad;
an adhesive layer disposed on one or more bottom surfaces of each of the front pad and the rear pad for secure attachment to the undergarment.

* * * * *